(12) United States Patent
Sommers et al.

(10) Patent No.: US 8,382,758 B1
(45) Date of Patent: Feb. 26, 2013

(54) METHOD FOR ALIGNING UPPER EXTREMITY BONES AND INSERTING GUIDE DEVICE

(76) Inventors: Mark Sommers, Beaverton, OR (US); Blake Matsuzaki, Hilsboro, OR (US); Matt Sucec, Portland, OR (US); Brandon Wedam, Hillsboro, OR (US); Michael McNamara, Anchorage, AK (US); Mikhail Polyakov, Portland, OR (US)

( * ) Notice: Subject to any disclaimer, the term of this patent is extended or adjusted under 35 U.S.C. 154(b) by 0 days.

(21) Appl. No.: 13/415,161

(22) Filed: Mar. 8, 2012

(51) Int. Cl.
*A61B 17/00* (2006.01)
*A61F 4/00* (2006.01)
*A61F 5/04* (2006.01)

(52) U.S. Cl. .......................... 606/59; 606/54
(58) Field of Classification Search .................... 606/58, 606/59, 96, 98, 104, 105
See application file for complete search history.

(56) References Cited

U.S. PATENT DOCUMENTS

| | | | |
|---|---|---|---|
| 4,848,327 A | 7/1989 | Perdue | |
| 6,589,242 B1 | 7/2003 | Feiler et al. | |
| 6,695,841 B2 | 2/2004 | Feiler et al. | |
| 7,674,264 B2 | 3/2010 | Feiler et al. | |
| 7,887,545 B2 | 2/2011 | Fernandez et al. | |
| 8,182,483 B2 * | 5/2012 | Bagnasco et al. | 606/58 |

* cited by examiner

*Primary Examiner* — Eduardo C. Robert
*Assistant Examiner* — Christina NegrelliRodriguez
(74) *Attorney, Agent, or Firm* — Peter A Haas Esquire LLC

(57) ABSTRACT

An elevator assembly includes a vertical shaft carrying a lower horizontal jaw held in fixed position relative to the shaft. The shaft carries an horizontally extending dorsal plate that can adjust vertically relative to the lower jaw by means of the vertical shaft. A targeting wing couples to the elevator shaft and is selectively adjustable up and down along the shaft by means of an elevator adjustment screw. The targeting wing includes at least one horizontal slot that is adapted to slideably receive a soft tissue protector and needle assembly. The soft tissue protector can lock in the slot of the targeting wing by rotating its oval body about 90-degrees clockwise.

12 Claims, 5 Drawing Sheets

METHOD FOR ALIGNING UPPER EXTREMITY BONES AND INSERTING GUIDE DEVICE

BACKGROUND

The present invention generally relates to devices the align bones of the human upper extremities and guide insertion of pins, screws, and the like in these bones More specifically, the present invention relates to devices for aligning the Scaphoid and Lunate bones of a human wrist and a guide for inserting a percutaneous guide wire and placement of a screw to hold anatomical reduction of the scaphoid and lunate after disruption or damage of the scapholunate interosseous ligament has occurred.

Until recently orthopedic surgeons had inadequate tools to assist in wrist surgeries, particularly related to scapholunate instability and non-displaced scaphoid fractures. Prior to that, such repairs to the upper extremity required considerable skill on the part of the surgeon and an even greater amount of guess work and luck.

Currently, Acumed LLC of Hillsboro, Oreg., manufactures a Scaphoid Targeting Guide that greatly improves the state of the art. The Acumed device facilitates percutaneous guidewire placement for non-displaced fractures of the scaphoid. The guide device enables a screw to be accurately and precisely placed down the central axis of the scaphoid. Further, the Acumed device includes a clamping feature to hold the patient's hand firmly in position while moving from anterior-posterior views to lateral views for imaging. And, under fluoroscopy, the device assists the surgeon better align the guide relative to proper scaphoid positioning.

A similar device is described in U.S. Pat. No. 7,674,264 issued on Mar. 9, 2010 to Feiler et al. Therein, a surgical appliance for assisting in the repair of a fractured bone, such as a scaphoid bone, is disclosed. The device includes a first and second adjustably interconnected and spaced apart limb clamping jaws that are transparent to x-rays and are movable relative to each other along its vertical axis. A rotatable disk carried by the first jaw has a plurality of bores angularly disposed thereon. The bores enable selective alignment of a guide wire for percutaneous drilling into the fractured bone.

Feiler et al., in U.S. Pat. No. 6,695,841 issued on Feb. 24, 2004, described another percutaneous scaphoid fixation method and guide wire alignment device having two opposed clamping plates. In the '841 patent, Feiler et al. teach internal fixing a fractured bone by placing the limb in an x-ray-transparent stabilizing clamp. The clamp includes a pair of opposed relatively movable jaws between which the wrist is inserted. The jaws are closed over the dorsal and palmar sides of the wrist, which is held in position between the clamps for imaging and subsequent use to align a guide wire.

Yet another clamping device and method of use is described again by Felier et al. in U.S. Pat. No. 6,589,242 issued on Jul. 8, 2003. In this version a jig inserts between the opposing clamping plates. The jig consists of a solid block that is pivotally and slidably mounted on a rod that extends through the dorsal clamp. The block is locked into relative position and orientation by a thumbscrew and a plurality of holes on the block enable a guide wire to be aligned relative the hand that is clamped between the two jaws.

These known clamping devices and other such similar iterations of devices and associated methods for aligning bones of the wrist and inserting guide wires have some limitations. Such limitations include the inability to target two bones simultaneously, they do not lock onto the bones targeted, just the exterior of the wrist. Also these devices are not completely stable to the targeted bones when the wrist is moved.

Other teachings of the prior art include non-clamping guide devices. These devices are generally characterized by having an insertion-point guide end and an oppositely spaced targeting end. These two ends are typically coupled by a bridging like mechanism that is designed to clear the external anatomy of a patient. One such representative non-clamping guide device of the prior art includes an apparatus and procedure for blind alignment of fasteners extended through transverse holes in an orthopedic locking nail, as described by Perdue in U.S. Pat. No. 4,848,327 issued on Jul. 18, 1989. Therein Perdue discloses a jig requiring considerable surgical skill to set in precise reference or indexing position to facilitate forming holes through the skin and bone of a body location precisely coaxially aligned. The jig includes an elongated I-beam that suspends two oppositely spaced and downward extending, vertically mounted tracking guides.

Yet another aiming guide is described by Fernandez et al. in U.S. Pat. No. 7,887,545 issued on Feb. 15, 2011. Therein an elongated aiming arm supports an aiming portion with two coplanar transverse holes. Again, the aiming arm is adapted for external use to span over a portion of the patient's anatomy. Relative positioning is accomplished by coupling the aiming arm to an intermedullary nail before it is inserted in the bone. Then, as the nail penetrates the bone, the aiming arm moves correspondingly exterior to the body.

One problem of such external guides that do not use a pair of clamping jaws is that they are time-consuming to align precisely, require considerable skill by the user to make precise alignments and are easy to move out of position.

Thus, there remains a need for an alignment guide and method of use that overcomes these limitations. Such an improved device and method should target two bones simultaneously and fix relative and directly to anatomical structure instead of locating by the exterior of the hand or wrist as currently taught in the art. Further, there is a need for a device that externally clamps to a patient's hand quickly, yet allows the surgeon to move the hand freely without worrying that the position of a targeting guide relative to the clamp will become mis-aligned or dislodged. Further, such a device should include a targeting guide that allows for precise external alignment of a guide wire relative to either the left or right hand's scaphoid and lunate bones, and further allow adjustment to the alignment guide when clamped relative to the external hand of the patient. Another need is for a guide that also protects the patient's soft tissue.

SUMMARY OF THE INVENTION

To overcome the limitations of the known art and to provide improved features never contemplated in the art, the present invention in its various contemplated embodiments includes a targeting device that externally clamps to a patient's hand quickly, yet allows the surgeon to move the hand freely without worrying that the position of a targeting guide relative to the clamp will become mis-aligned or dislodged. Further, the present invention includes a targeting guide that allows for precise external alignment of a guide wire relative to either the left or right hand's scaphoid and lunate bones, and further allows precision adjustment to the alignment guide when clamped relative to the external hand of the patient. Further, the present invention includes a soft-tissue protector.

In one preferred embodiment, the device of the present invention is well suited for use to place a guide wire into the central third of the Lunate bone in both the Posterior/Anterior view and the Lateral view. One key advantage to this device is that is allows targeting both the scaphoid and lunate bones in the central third in the Lateral view. The screw adjustment feature of the device makes this alignment of a guide wire relative to the targeted scaphoid and lunate bones much easier to locate over any existing methods and devices of the prior art.

The present invention further includes a quick release mechanism that allows the user to clamp it to the patient's wrist while holding the reduction of the lunate bone. This provides stability to the device allowing the surgeon to move the arm freely without losing reduction of the lunate or losing the position of the targeting needle in the Dorsal/volar view. This advantage is better understood in context of the teachings of the prior art that require the patient's hand to be much more stationary because the targeted area is easily misaligned if the patient's hand moves relative to the guide.

Another feature of the present invention is a soft tissue protector. This can be locked into position when the surgeon has located the proper angle of trajectory in the posterior/anterior view and, thus locking in the scaphoid needle as well.

Yet another feature of the present invention is the scaphoid needle component, which helps prevent the guide wire from skiving off the scaphoid during initial insertion. Finally, when secured to the patients wrist with the sliding plate clamped and the lunate guide wire installed the device is lined up in the proper trajectory for the guide wire to cross the scaphoid and enter the lunate in a trajectory that is close to a true Lateral/Medial plane in relation to the wrist.

DRAWING

DESCRIPTION OF THE INVENTION

Figure 1:
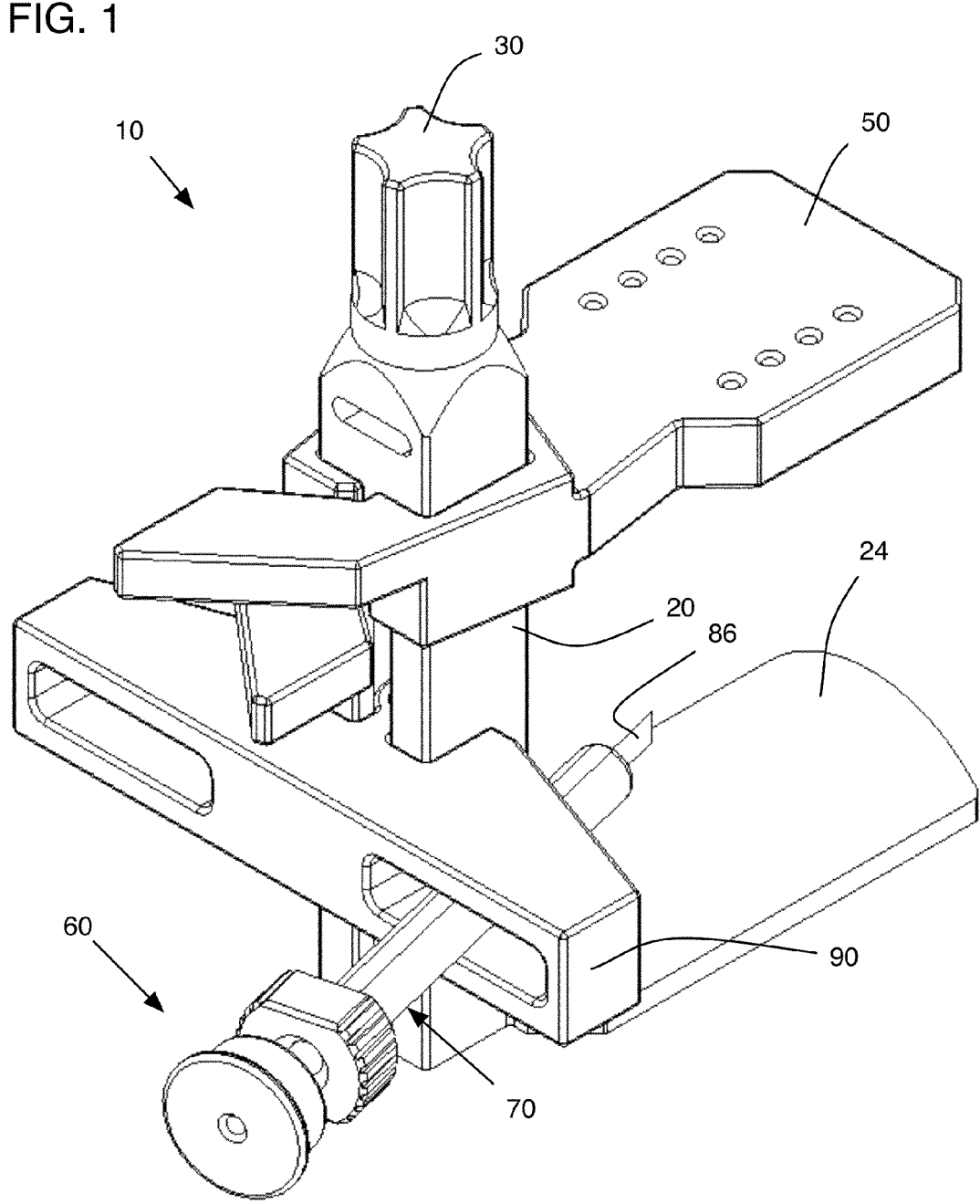
FIG. 1 is an offset frontal view of a preferred embodiment of the present invention.
Figure 2:
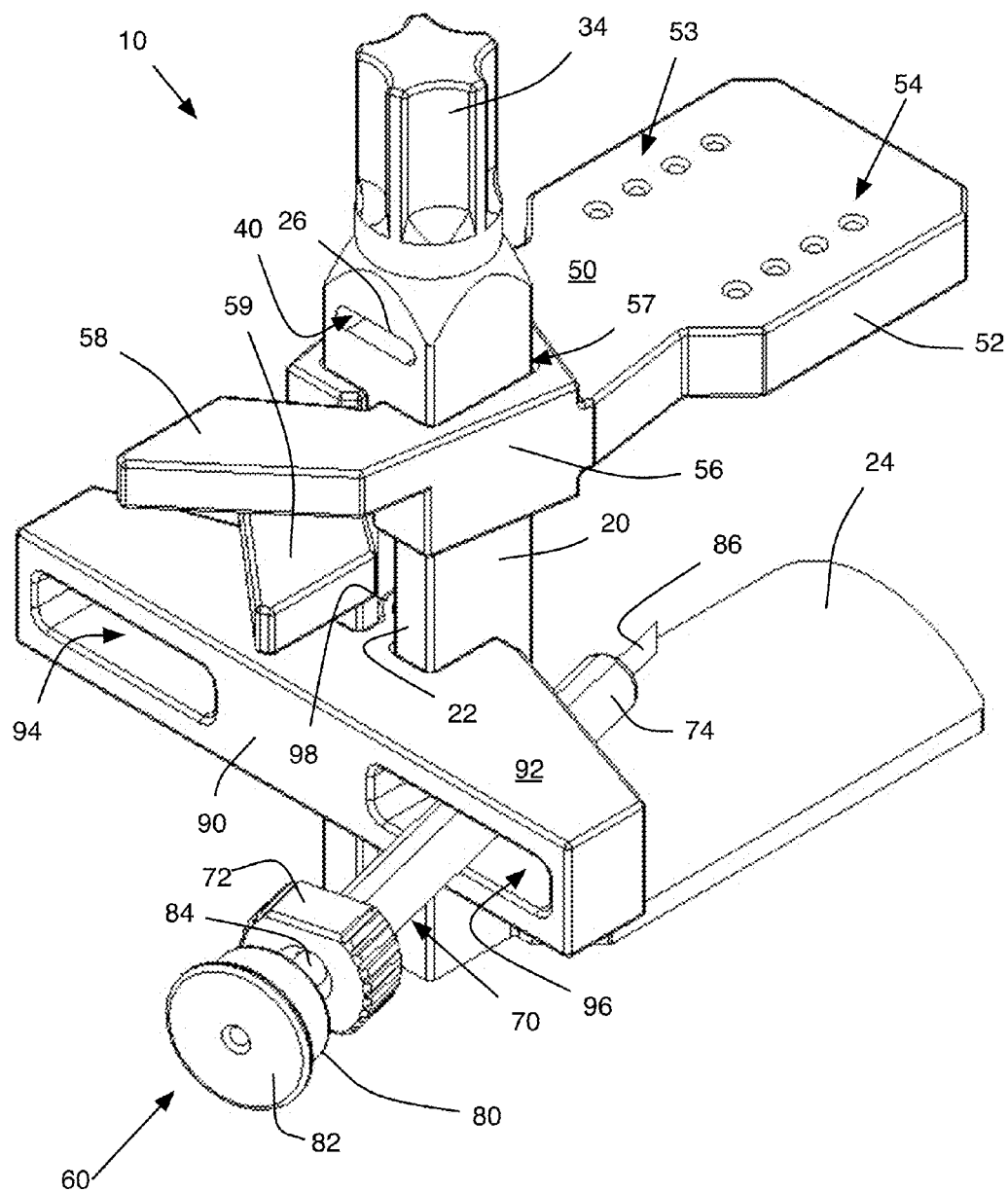
FIG. 2 is another offset frontal view of the embodiment of FIG. 1.
Figure 3:
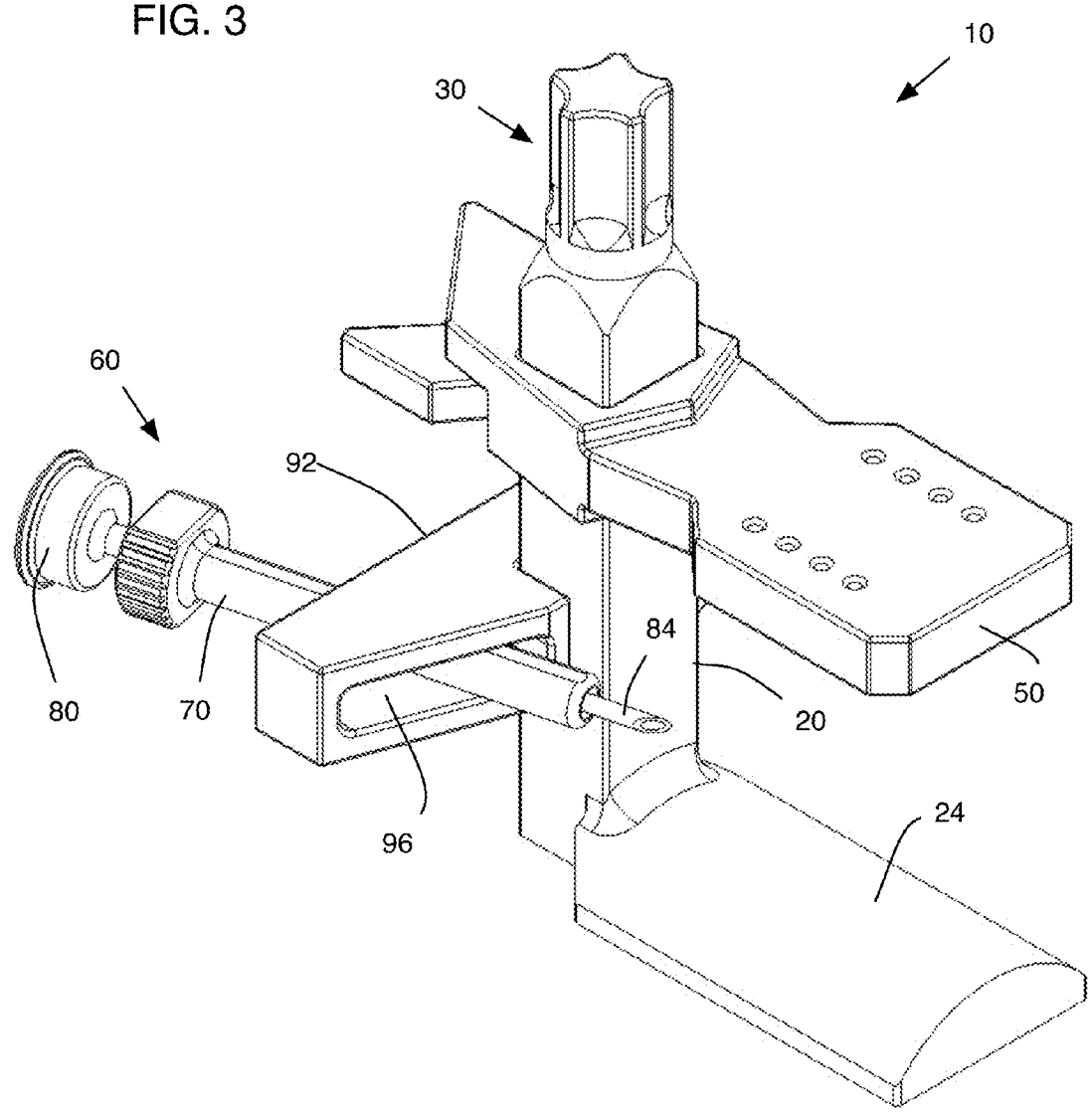
FIG. 3 is an offset back view of the embodiment of FIG. 1.
Figure 4:
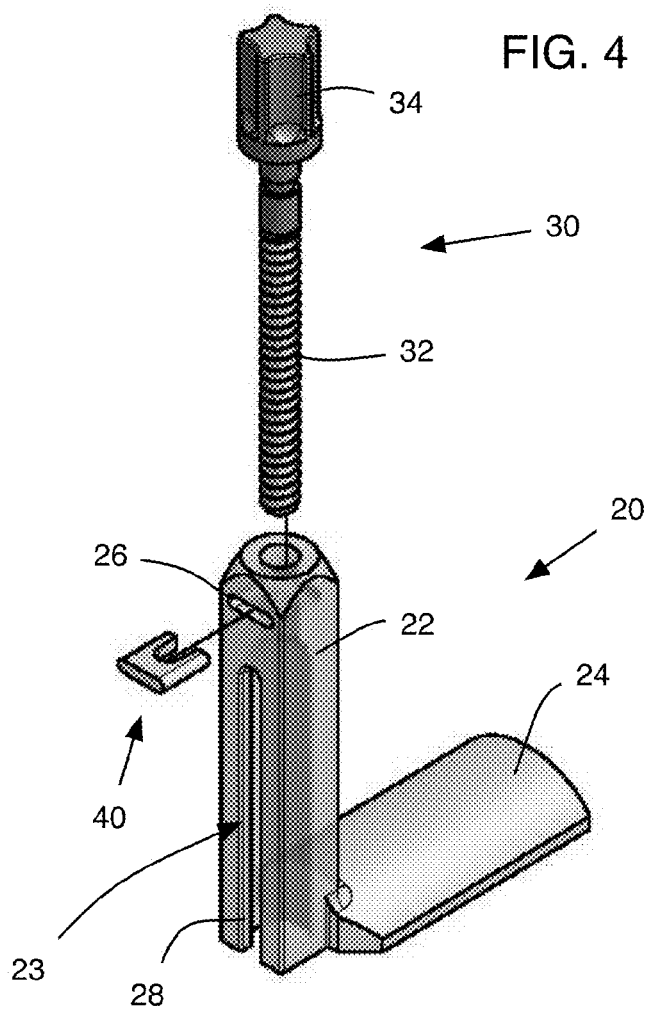
FIG. 4 is an offset front view of various components of the embodiment of FIG. 1.
Figure 5:
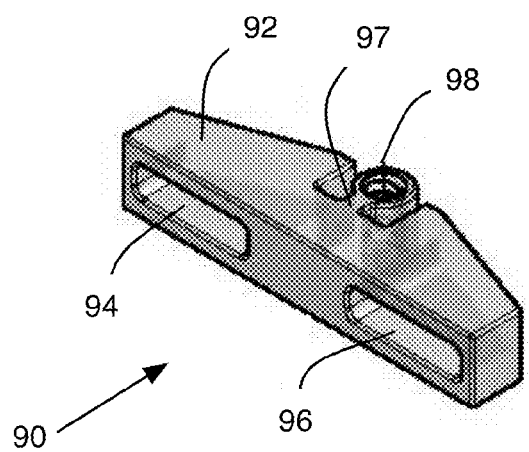
FIG. 5 is an offset front view of another component of the embodiment of FIG. 1.
Figure 6:
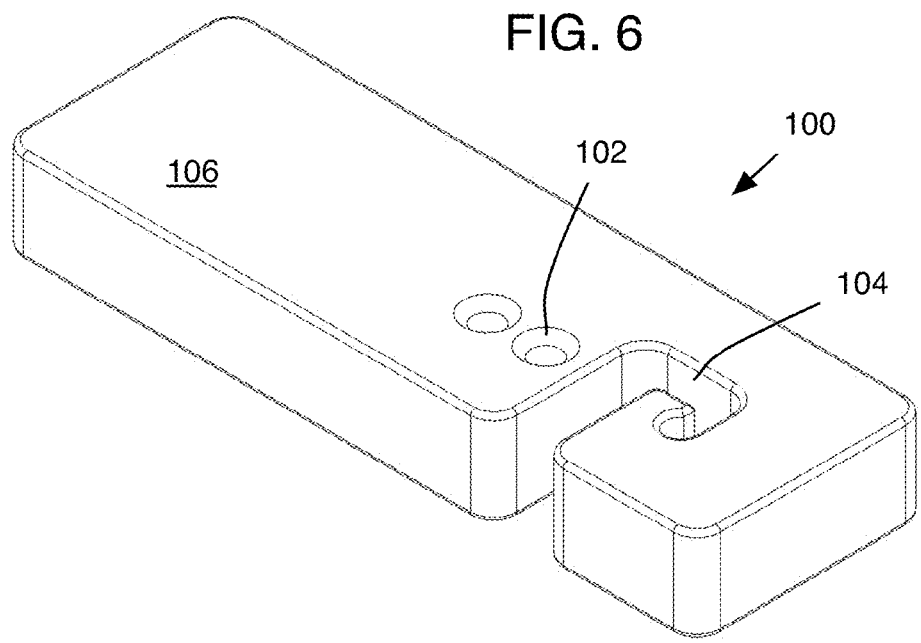
FIG. 6 is an offset top view of a component of an alternate embodiment of the present invention.

Possible preferred embodiments will now be described with reference to the drawings and those skilled in the art will understand that alternative configurations and combinations of components may be substituted without subtracting from the invention. Also, in some figures certain components are omitted to more clearly illustrate the invention.

A preferred embodiment of the present invention, as FIGS. 1-6 illustrate, includes a device 10 adapted to align bones of the human upper extremities and guide insertion of pins, screws, and the like in these bones. More specifically, the present invention relates to devices for aligning the Scaphoid and Lunate bones of a human wrist and a guide for inserting a percutaneous guide wire and placement of a screw.

This guide device 10 includes an elevator 20 consisting of a generally hollow and vertically arranged shaft 22. In this embodiment the shaft 22 has a rectilinear cross section when viewed from the top, with a corresponding rectilinearly shaped hollow center portion. However, other configurations of this vertical shaft are contemplated and would include, without limitation, oval, round, round with apposing flats, octagonal, hexagonal, and the like, for example. The vertical shaft 22 has an exterior wall arranged to define an interior channel—specifically, the vertical shaft has four vertical walls arranged at right angles to its adjacent wall to define a rectilinear hollow center portion that extends at least partially from the top to the bottom of the vertical shaft. This centrally disposed interior conduit 23 extends from one end of the shaft to its opposite end for ease of manufacturing, but could—in other contemplated embodiments—extend only a portion of the length of the vertical shaft. Additionally, the shaft, on one of its exterior side walls, includes a vertical slot 28 extending for at least an intermediate portion of a vertical length of the shaft. Coupled to, or otherwise formed and disposed or supported by, at a lower end of the shaft 22, the elevator 20 includes a horizontally extending lower jaw 26.

The elevator 20 is adapted to receive an elevator screw 30, which arranges at the top end of the shaft 22 and is at least partially inserted in the interior conduit 23. The elevator screw 30 includes a head portion having a thumb-adjust head 34 and a threaded rod portion 32 extending from the head. The threaded-rod portion 32 is adapted to fit inside the interior conduit of the elevator's vertical upright shaft with clearance so that a carrier of the targeting wing (described below) can be inserted in the shaft and ride the threaded-rod portion whereby rotation of the head 34 in one direction (i.e. clockwise) causes the targeting wing to move vertically upward relative to the elevator shaft 22 and rotation in an opposite direction (i.e. counter-clockwise) causes the targeting wing to move in an opposite, downward, direction.

The guide 10 further includes a targeting wing 90 slideably mounted to the elevator 20 by means of a targeting carrier 98 adapted to thread to the threaded-rod portion 32 of the elevator screw 30, the carrier 98 further adapts to slideably insert inside the interior conduit 23 of the elevator's shaft. The carrier further comprising a neck 97 having a portion extending horizontally from the elevator's shaft extending beyond the slot 28 and shaft wall. The neck 97 connects the carrier 98 to the targeting wing body 92. The body 92 comprises at least one targeting slot 94, and preferably two slots 94 and 94 symmetrically arranged and disposed horizontal relative to the vertical elevator upright shaft.

In one embodiment, the targeting wing 90 slideably mounts or couples to the elevator 20 by means of a targeting carrier 98 adapted to selectively slide in the vertical slot of the elevator. This feature is better illustrated in FIGS. 4 and 5. Then, using the elevator screw 34, the targeting wing can be precisely positioned in a vertical axis. A retainer 40 then locks the screw in relative position in the shaft 22. The carrier 98 slides in the interior channel 23 and extends outside the slot 28. Thus, the targeting wing can be located relative to the fixed bottom jaw 24.

The guide 10 further includes a needle assembly 60 adapted to slideably and rotatably engage the at least one targeting slot (94 or 96) of the targeting wing assembly 90. Further, the needle assembly 60 includes a soft tissue protector 70 and a needle 86 inserted into a needle handle 80 having a retaining arm 84 and oversized head 82. The needle arm slideably inserts inside the soft tissue protector 70. And, the soft tissue protector 70 has an elongated ovoid cross section and is adapted to rotate from a first position while in the slot 94 (or 95) that allows the soft tissue protector 70 to be positioned to a second position about 90-degrees from the first position and in the second position an interference fit is created between the soft tissue protector 70 and the corresponding slot 94 or 96 to temporarily lock or fix the position of the soft tissue protector relative to the targeting wing 90.

The guide 10 also includes a selectively positionable sliding plate 50. The sliding plate arranged parallel to the lower jaw 24 of the elevator 20, but is selectively movable up and down along the elevator shaft 22 from at least one position to a second position. The sliding-plate 50 is carried by an exterior portion of the vertical upright shaft 22. The sliding plate 50 includes a horizontally extending upper jaw 52 coupled to or carried by a neck portion 56. The neck 56 defines an opening or slot 57. This slot 57 adapts to selectively engage and disengage the exterior portion of the vertical upright shaft 22 by means of a quick-release mechanism. The quick release mechanism in one preferred embodiment consists of cooperating left and right scissor clamps 58 and 59 coupled to or otherwise carried by the neck portion extending horizontally away from the direction of the sliding plate jaw 52. The jaw 52 further includes at least one, and preferably two sets of lunate-guide holes 53 and 54. The pair of scissors clamps adapt to be able to be squeezed together, which causes the slot 57 to enlarge enabling the sliding plate to slide vertically relative to the elevator 20. Releasing the clamps 58 and 59 returns the clamps to their resting position, which causes the slot 57 to have an interference fit with the exterior of the shaft 22. This, in turn, temporarily fixes the sliding plate relative to the elevator.

The guide 10 also includes a clip 100. The clip positions relative to the elevator 20 by means of guide wires that are inserted into the wrist of the patient, one in the lunate and one in the scaphoid as would be generally understood by those skilled in the art. As such, there is no direct mechanical link to the elevator with the scaphoid wire. The clip 100 further adapts to hold at least one guidewire adapted to enable holding the correct anatomical position of the Scaphoid and Lunate. And, the clip positions on the at least one guidewire at a distance remote from the sliding plate 50, which also carries the common guidewire by supporting the guide wire by any one of its corresponding aligning lunate-guide holes 53 or 54. See, for example, FIGS. 6 and 7.

Figure 7:
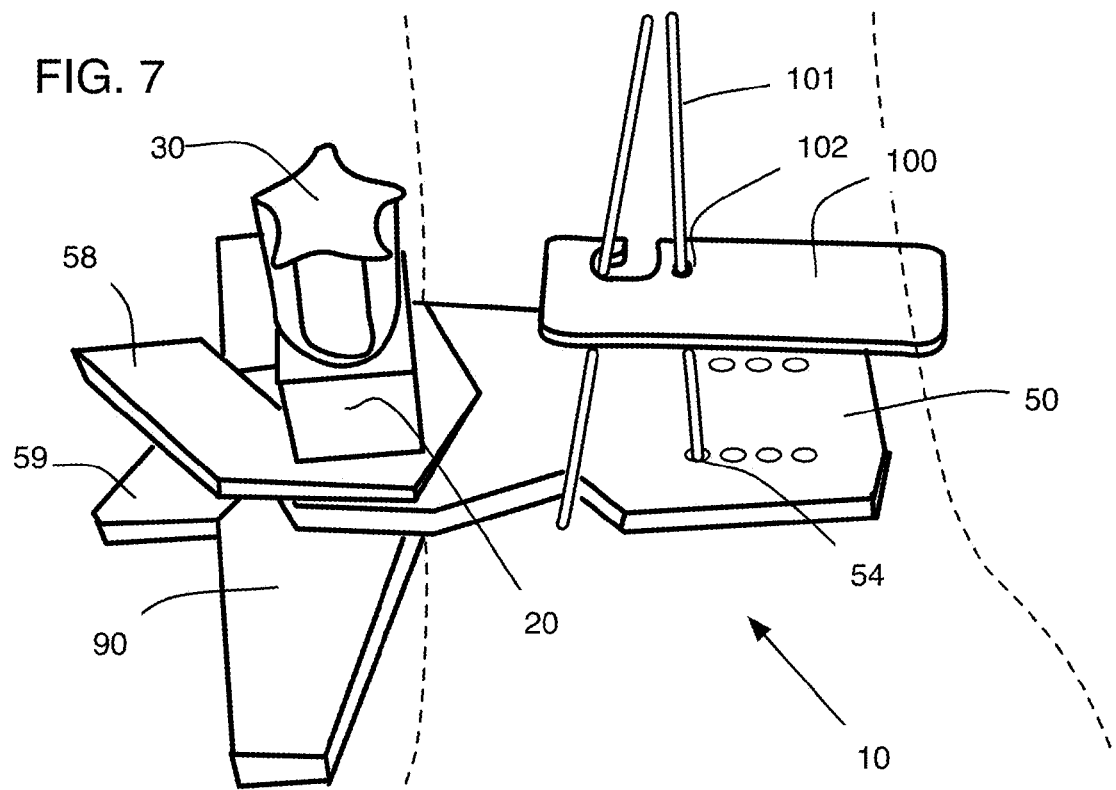
FIG. 7 is an offset to view of another embodiment of the present invention and illustrates the component of FIG. 6 in situ.

This device 10 as described above and illustrated in the figures is a part of a system of FIG. 7 and is adapted for use to align a Lunate bone in both the Posterior/Anterior view and the Dorsal/Volar view. This system is further understood in view of the method described below.

The device of the present invention in its various embodiments and as illustrated in the various figures of the drawing is well suited for use as a surgical guide 10 to align bones of the human upper extremities and guide insertion of pins, screws, and the like in these bones. More specifically, the present invention adapts well as a guide device for surgeons operating on the hand of a human patient and even more particularly to assist in aligning the Scaphoid and Lunate bones and as a guide for inserting a percutaneous guide wire and placement of a screw.

A contemplated method of the present invention begins with selecting a scapho-lunate guide wire and inserting it the radial side of the wrist through the scaphoid into the lunate. The starting point on the scaphoid is just distal to the tip of the radial styloid. Incise the skin, and then proceed with blunt dissection down to the level of the capsule. Recognize and protect the radial artery, vena comitante, and subcutaneous branch of the dorsal radial cutaneous nerve. A minimal radial styloidectomy may be necessary to access the scaphoid.

Next, the interval and rotation of the scaphoid and lunate should be anatomically reduced prior to the repair/fixation of the scapholunate joint. Place a 0.045" to 0.062" K-wire dorsally into the distal middle third of the lunate under fluoroscopy. Use an angle of approach that will leave the K-wire in a perpendicular orientation to the dorsal aspect of the wrist after the lunate is reduced to anatomical position. In the lateral view, place K-wire parallel to the dorsal volar lip of the lunate orientation.

Now, select the device 10 of the present invention and place the guide elevator body 24 under the patient's wrist against the volar surface of the wrist. Snug the elevator body 20 against or flush with the radial side of the wrist. This is accomplished by squeezing together the cooperating scissor clamp left 58 and right 59, which enlarges the slot making the downward travel of the sliding plate possible. When the clamps 58 and 59 are released, surface friction prevents the sliding plate from sliding up and down vertically on the elevator shaft 20.

Select a lunate hole 53 (or 54 depending on left or right wrist) on the corresponding side of the dorsal plate 50 that still allos the elevator 20 to sit flush with the radial side of the wrist and slide the sliding plate 50 downward until it is snug to the dorsal aspect of the wrist.

Place a 0.045" K-wire into the waist of the scaphoid under fluoroscopy as the second joystick to reduce the SL interval into its anatomical position. Placement of scaphoid joystick will be surgeon's preference as long as it will not be in the path of the SL fixation guide wire. It is often placed from distal to proximal to reduce a flexed scaphoid if needed. Use the supplied S-Clip 100 or a pair of Kocher's clamps to bring the joysticks together and hold anatomical reduction of the scaphoid and lunate. The scaphoid should be rotated back into normal rotation without excessive bending in the k-wire. If excessive bending occurs in the 0.045" K-wire, the scapholunate interval is probably not dynamic or "easily reducible" and a salvage option should be considered instead.

With the guide securely fashioned to the wrist and the SL anatomically reduced; view the wrist under fluoroscopy in the Radial/Ulnar direction. Insert the soft tissue protector 70 into the appropriate slot 94 or 96 in the targeting wing 90. Advance the soft tissue protector 70 into the incision down to the scaphoid capsule or against skin if using percutaneously. When the correct trajectory is located, lock the soft tissue protector into position by rotating it clockwise using the head 72, which translates the ovoid body conduit 74 from the flatter clearance position that easily slides in the slot, to a taller, interference position that wedges in the slot.

Insert the scaphoid needle assembly 60 through the soft tissue protector 70. Use the dial 30 at the top of the Guide Elevator 20 to get the correct Lateral position, using the radio-opaque needle under fluoroscopy as a marker. Clockwise moves the targeting wing in the dorsal direction and counterclockwise moves the wing in the volar direction. The correct location in the Lateral view will be centered in the middle ⅓rd of the lunate.

Then rotate the wrist back to the PA view and use fluoroscopy to align the approach of the guide wire. The guide wire should be placed centrally in the scaphoid and lunate and exit the lunate at the most ulnar proximal corner as shown; it should not pass through the scaphocapitate or lunacapitate joint spaces. Rotate the scaphoid needle 86 so the tip is at its most proximal position and then lightly press the scaphoid needle assembly 60—by pushing on the head 80—into the scaphoid. The scaphoid needle in the correct rotation helps to prevent the guide wire from skiving off the scaphoid.

Confirm you have the correct trajectory in PA and Lateral views under fluoroscopy and place a 0.045" Guide wire into the scaphoid needle. Advance the guide wire into the scaphoid and lunate, checking under fluoroscopy periodically to ensure the correct path. Continue to advance the guide wire per surgeon's discretion.

Although the invention has been particularly shown and described with reference to certain embodiments, it will be understood by those skilled in the art that various changes in form and detail may be made without departing from the spirit and scope of the invention.

We claim:

1. A guide device comprising:
   an elevator comprising a vertical upright shaft, the shaft comprising a centrally disposed interior conduit extending for at least a portion of its interior volume and the elevator further comprising a vertical slot extending for at least an intermediate portion of a vertical length of the shaft, and the vertical upright shaft supporting a horizontally extending lower jaw;
   a targeting wing slideably mounted to the elevator by means of a targeting carrier adapted to selectively slide in the vertical slot of the elevator, the targeting wing further adapted to selectively hold a fixed position relative to the lower jaw of the elevator by means of a variable select mechanism and the targeting wing comprising at least one targeting slot disposed horizontal relative to the elevator's vertical upright shaft; and
   a sliding plate carried by an exterior portion of the vertical upright shaft, the sliding plate adapted to selectively slide vertically on the exterior portion of the vertical upright shaft and lock into at least one desired position on the vertical upright shaft and the sliding plate further comprising
      a horizontally extending upper jaw coupled to a neck portion defining a slot adapted to selectively engage and disengage the exterior portion of the vertical upright shaft by means of quick release mechanism coupled to the neck portion.

2. The guide device of claim 1 further comprising:
   a needle assembly adapted to slideably and rotatably engage the at least one targeting slot of the targeting wing assembly.

3. The guide device of claim 1 further comprising:
   a clip adapted to hold at least one guidewire adapted to enable holding the correct anatomical position of the Scaphoid and Lunate; and
   the clip positioned on the at least one guidewire at a distance remote from the sliding plate, the at least one guidewire slideably inserted through any one of the at least one lunate-guide hole.

4. The guide device of claim 1 further comprising:
   a soft-tissue protector adapted to slide in the at least one lateral slot when the soft-tissue protector is arranged in a first orientation, and the soft-tissue protector adapted to selectively rotate about 90-degrees while in the slot to a second position that secures the soft-tissue protector in relative position with the slot, and
   a needle assembly adapted to slideably insert inside the soft tissue protector, the needle assembly comprising a head end and an oppositely disposed needle.

5. The targeting wing of claim 4 wherein:
   the carrier further adapts to slideably mount to the interior conduit of the elevator's shaft, the carrier further comprising a neck having a portion extending horizontally from the elevator's shaft, the neck supporting a body, the body comprising at least one targeting slot disposed horizontal relative to the vertical elevator upright shaft.

6. The targeting wing of claim 1 wherein the variable select mechanism further comprises:
   an elevator screw comprising a thumb-adjust head and a threaded rod portion extending from the head, the threaded-rod portion adapted to fit inside the interior conduit of the elevator's vertical upright shaft.

7. The needle assembly of claim 1 further comprising:
   a soft tissue protector and a needle carried by the soft tissue protector, the soft tissue protector further comprising, at a distal end, a horizontally disposed hollow shaft adapted to slideably receive a portion of the needle and at a proximal end an oval head adapted to arrange in first position in the at least one targeting slot whereby the needle assembly can slide horizontally left to right and horizontally in and out relative to the slot, and the oval head adapted to arrange in a second position in the at least one targeting slot whereby horizontal movement is prevented;
   the needle further comprising a head extending outside the proximal end of the soft tissue protector.

8. The sliding plate of claim 1 further comprising:
   at least one lunate-guide hole.

9. A system adapted for use to hold reduction of anatomically reduced lunate and scaphoid bones in both a posterior/anterior view and a lateral view, the system comprising:
   a joystick clip adapted to selectively engage at least one joystick wire or K-wire;
   a guide device comprising
   an elevator comprising a vertical upright shaft, the shaft comprising a centrally disposed interior conduit extending for at least a portion of its interior volume and the elevator further comprising a vertical slot extending for at least an intermediate portion of a vertical length of the shaft, and the vertical upright shaft supporting a horizontally extending lower jaw;
      a targeting wing slideably mounted to the elevator by means of a targeting carrier adapted to selectively slide in the vertical slot of the elevator, the targeting wing further adapted to selectively hold a fixed position relative to the lower jaw of the elevator by means of a variable select mechanism and the targeting wing comprising at least one targeting slot disposed horizontal relative to the vertical elevator upright shaft;
      a needle assembly adapted to slideably and rotatably engage the at least one targeting slot of the targeting wing assembly; and
      a sliding plate carried by an exterior portion of the vertical upright shaft, the sliding plate adapted to selectively slide vertically on the exterior portion of the vertical upright and lock into at least one desired position on the vertical upright.

10. A method for aligning a scaphoid and lunate bones of a wrist, the method comprising:
    providing the system of claim 9;
    selecting a scapho-lunate guide wire and inserting it a radial side of the wrist through the scaphoid into the lunate;
    reducing anatomically the interval and rotation of the scaphoid and lunate by placing a guidewire dorsally into the distal middle third of the lunate using an angle of approach that will leave the guidewire in a perpendicular orientation to the dorsal aspect of the wrist after the lunate is reduced to anatomical position;
    selecting a guide device of the system and placing the guide elevator lower jaw under the wrist against the volar surface of the wrist;
    snugging the elevator body against or flush with the radial side of the wrist and placing the sliding plate against the exterior surface of the wrist;

selecting a lunate hole on the corresponding side of the sliding plate; and placing a guidewire into the waist of the scaphoid as the second joystick to reduce the SL interval into its anatomical position.

11. The method of claim 10 further comprising:

advancing the soft tissue protector;

inserting the needle into the soft tissue protector without piercing the scaphoid;

adjusting the Dorsal/Volar position of the soft tissue protector to align the needle centrally to the lunate by moving the targeting wing with the elevator screw in the lateral view;

switching to the PA direction and align the needle direction to ensure guide wire will pass through scaphoid and lunate;

locking the soft tissue protector in the slot by rotating.

12. The method of claim 10 further comprising:

pushing on the head of the needle assemble so the needle enters into the scaphoid; and placing a guidewire into the scaphoid needle and advancing the guide wire into the scaphoid and lunate, checking under fluoroscopy periodically to ensure the correct path.

* * * * *